(12) United States Patent
Brightbill

(10) Patent No.: US 7,008,442 B2
(45) Date of Patent: Mar. 7, 2006

(54) VASCULAR SEALANT DELIVERY DEVICE AND SHEATH INTRODUCER AND METHOD

(75) Inventor: Jerry Brightbill, Newton, MA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 346 days.

(21) Appl. No.: 10/348,406

(22) Filed: Jan. 20, 2003

(65) Prior Publication Data

US 2004/0143290 A1 Jul. 22, 2004

(51) Int. Cl.
*A61B 17/58* (2006.01)

(52) U.S. Cl. .................................................... 606/213

(58) Field of Classification Search .......... 606/213–215; 604/57, 59, 60, 96.01, 164.02, 164.03, 164.1, 604/167.02, 167.6, 168.01
See application file for complete search history.

(56) References Cited

U.S. PATENT DOCUMENTS

| | | | | | |
|---|---|---|---|---|---|
| 4,364,392 | A | | 12/1982 | Strother et al. ............. 128/325 |
| 5,665,107 | A | * | 9/1997 | Hammerslag ............... 606/214 |
| 5,725,551 | A | * | 3/1998 | Myers et al. ................ 606/213 |
| 5,782,860 | A | | 7/1998 | Epstein et al. .............. 606/213 |
| 6,017,359 | A | * | 1/2000 | Gershony et al. ........... 606/213 |
| 6,033,427 | A | | 3/2000 | Lee ............................. 606/213 |
| 6,056,768 | A | * | 5/2000 | Cates et al. ................. 606/213 |
| 6,120,480 | A | | 9/2000 | Zhang et al. ................ 604/164 |
| 6,287,323 | B1 | | 9/2001 | Hammerslag ............... 606/214 |
| 2002/0165528 | A1 | | 11/2002 | Edwards et al. |
| 2003/0109866 | A1 | | 6/2003 | Edwards et al. |

FOREIGN PATENT DOCUMENTS

| | | |
|---|---|---|
| EP | 0241038 A2 | 10/1987 |
| EP | 0241038 A3 | 10/1987 |
| EP | 0539237 A1 | 4/1993 |

* cited by examiner

*Primary Examiner*—Sharon Kennedy
(74) *Attorney, Agent, or Firm*—Forrest Gunnison (57) ABSTRACT

A sheath introducer is inserted through the skin and into a body lumen, e.g., the femoral artery, for a medical procedure. Upon completion of the medical procedure, the sheath introducer is partially withdrawn from the body lumen so that at least one through-wall hole in a body region of the sheath introducer is positioned outside the body lumen, but under the skin. An opening in a distal end tip of the sheath introducer is sealed so that no blood is flowing into the sheath introducer the after sheath introducer is partially withdrawn. A surgical sealant is injected into the sheath introducer and flows out of the at least one through-wall hole and surrounds the access site. After injection of the surgical sealant, the sheath introducer is removed. The surgical sealant seals the puncture and minimizes any blood flow from the body lumen through the puncture.

16 Claims, 9 Drawing Sheets

VASCULAR SEALANT DELIVERY DEVICE AND SHEATH INTRODUCER AND METHOD

BACKGROUND OF THE INVENTION

1. Field of the Invention

The present invention relates generally to closure devices for puncture sites in a body and more particularly to closure of puncture sites associated with percutaneous access to blood vessels in a human body or an animal body associated with introduction of a device into the blood vessel to accomplish a medical procedure.

2. Description of Related Art

Techniques for introducing a sheath introducer into a body lumen for a subsequent introduction of a device used to perform a medical procedure are well known. Introduction of the sheath introducer produces a puncture in the body lumen, e.g., a puncture in the femoral artery, at the access site.

At the conclusion of the medical procedure, the device is withdrawn through the sheath introducer and then the sheath introducer is withdrawn through the skin and from the body lumen. Various devices have been suggested for closing the puncture wound left in the body lumen. The devices are either complex, or rely upon techniques to isolate the puncture that are not reliable. While the problem of closing the puncture wound is recognized, a reliable, safe, easy to use device and method are still needed.

SUMMARY OF THE INVENTION

According to one embodiment of the present invention, a structure includes a sheath introducer having a distal end tip. The sheath introducer also includes a body region having a wall bounded by an outer wall surface of the sheath introducer and by an inner wall surface of the sheath introducer.

The body region is oriented about a longitudinal axis of the body region and is at about a predefined distance from the distal end tip. The body region can have some longitudinal extent and so is located at about the predefined distance. The body region includes at least one through-wall hole extending from the outer wall surface to the inner wall surface. The at least one through-wall hole is included in a plurality of through-walls holes in the body region.

The through-wall hole has a longitudinal axis that is oriented at an angle to the longitudinal axis of the body region. In one embodiment of the through-wall hole, the angle is about a 90° angle. In another embodiment of the through-wall hole, the angle is other than a 90° angle.

In still another embodiment of the through-wall hole, the at least one through-wall hole has a uniform cross section along the longitudinal axis of the at least one through-wall hole. In yet still another embodiment of the through-wall hole, the at least one through-wall hole has a non-uniform cross section along the longitudinal axis of the at least one through-wall hole.

The structure also includes a dilator having a shaft with a distal end. A dilator plug is formed about the shaft and extends from about the distal end of the shaft to about a predefined distance from the distal end of the shaft. Following insertion of the dilator into the sheath introducer, the dilator plug forms a seal in the distal end of the sheath introducer. The predefined distance from the distal end of the shaft is selected so that the dilator plug does not block the at least one through-wall hole.

The structure further includes a balloon clamp catheter extending through the sheath introducer. The structure also includes a guidewire extending through the sheath introducer. A surgical sealant delivery system is coupled to the sheath introducer to inject a surgical sealant into the sheath introducer. The sheath introducer includes a plurality of depth indicators on the outer surface.

A method for sealing a puncture of a body lumen created by using a sheath introducer plugs a distal end tip of a sheath introducer having a through-wall hole. The sheath introducer is positioned so that the through-wall hole is outside a body lumen and a surgical sealant is injected into the sheath introducer that in turn flows out the at least one through-wall hole.

The method also includes blocking the body lumen using a balloon clamp catheter. The sheath introducer is removed from the body lumen following the injecting. The balloon clamp catheter is removed from the body lumen after the sheath introducer is removed.

BRIEF DESCRIPTION OF THE DRAWINGS

In the drawings and the following detailed description, elements with the same reference numeral are the same or equivalent elements. Also, the first digit of a reference numeral for an element is the figure number of the figure in which that element first appears.

DETAILED DESCRIPTION

Figure 1A:
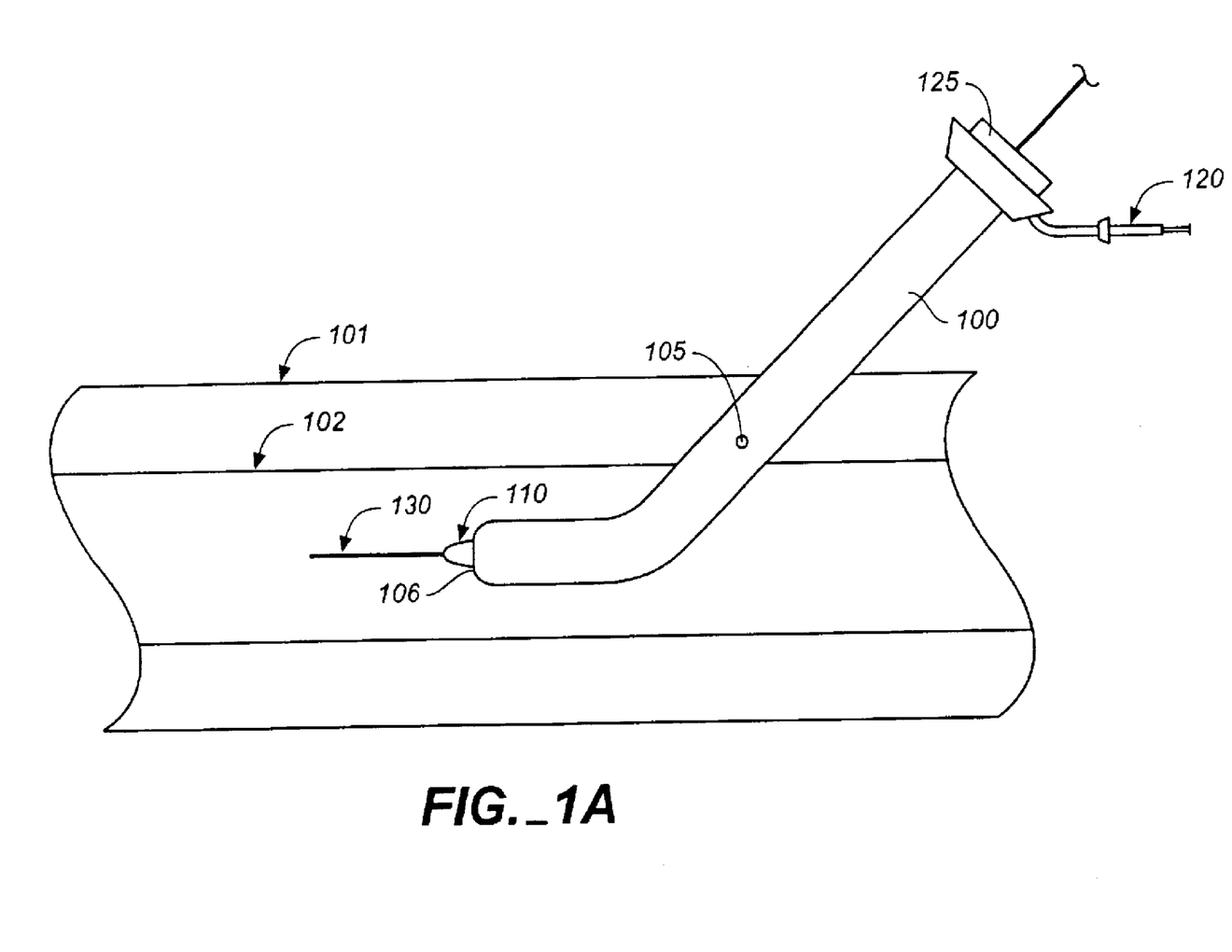
FIG. 1A is an illustration of a system used to inject a surgical sealant exterior to a puncture in a body lumen with the system positioned for sealant injection.

According to one embodiment of the present invention, a sheath introducer 100 (FIG. 1A) is inserted through skin 101 and into a body lumen 102, e.g., the femoral artery, for a medical procedure. Upon completion of the medical procedure, sheath introducer 100 is partially withdrawn from body lumen 102 so that at least one through-wall hole 105 in a body region of sheath introducer 100 is positioned outside body lumen 102, but under skin 101.

Figure 1B:
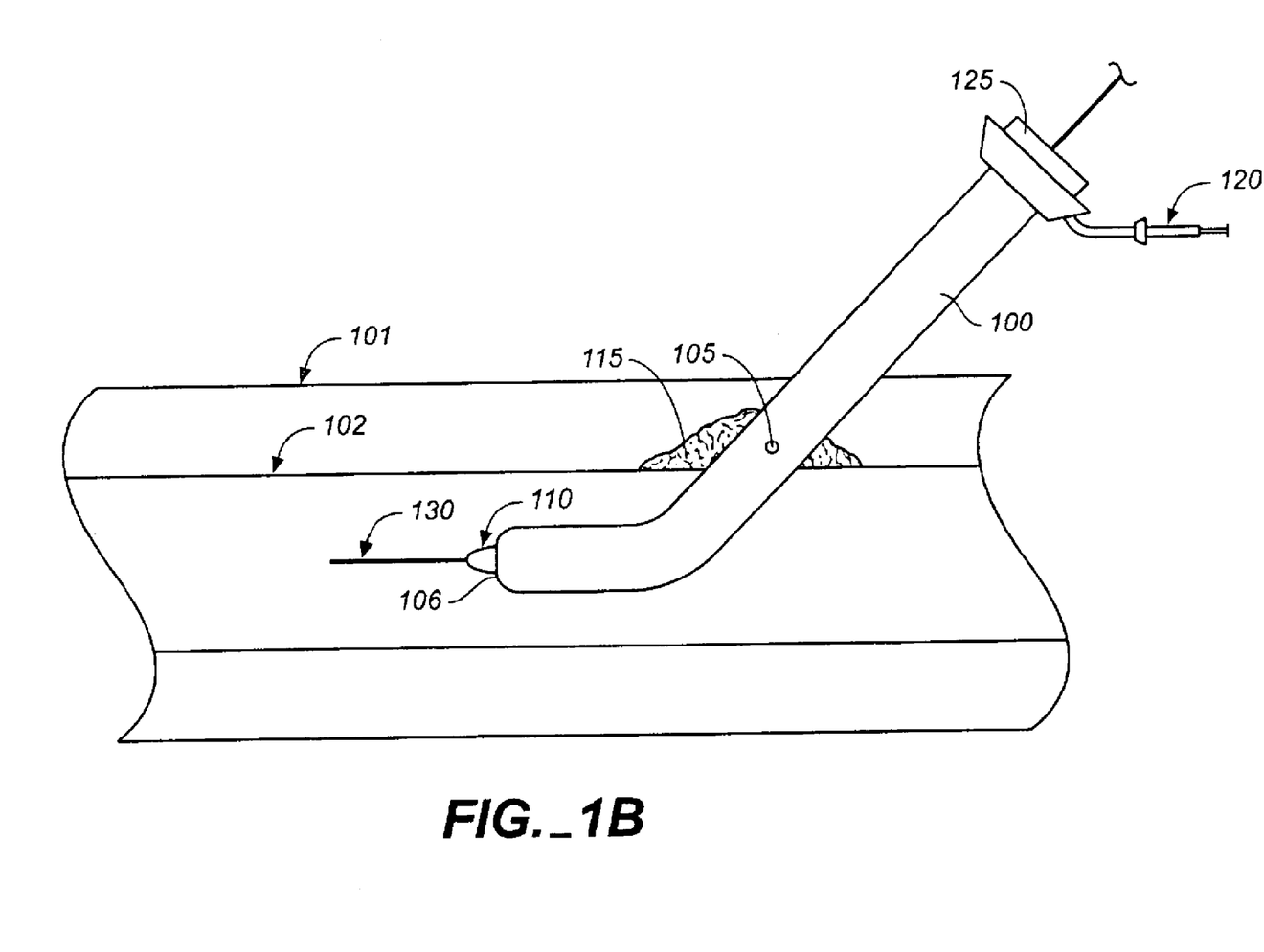
FIG. 1B illustrates the system of FIG. 1A following injection of the surgical sealant.

An opening in a distal end tip 106 of sheath introducer 100 is sealed by a plug 110 so that no blood is flowing into sheath introducer 100 after sheath introducer 100 is partially withdrawn. A surgical sealant is injected into sheath introducer 100 by a surgical sealant injection system 120. Surgical sealant 115 flows out of at least one through-wall hole 105 and surrounds the access site. (FIG. 1B.)

Figure 1C:
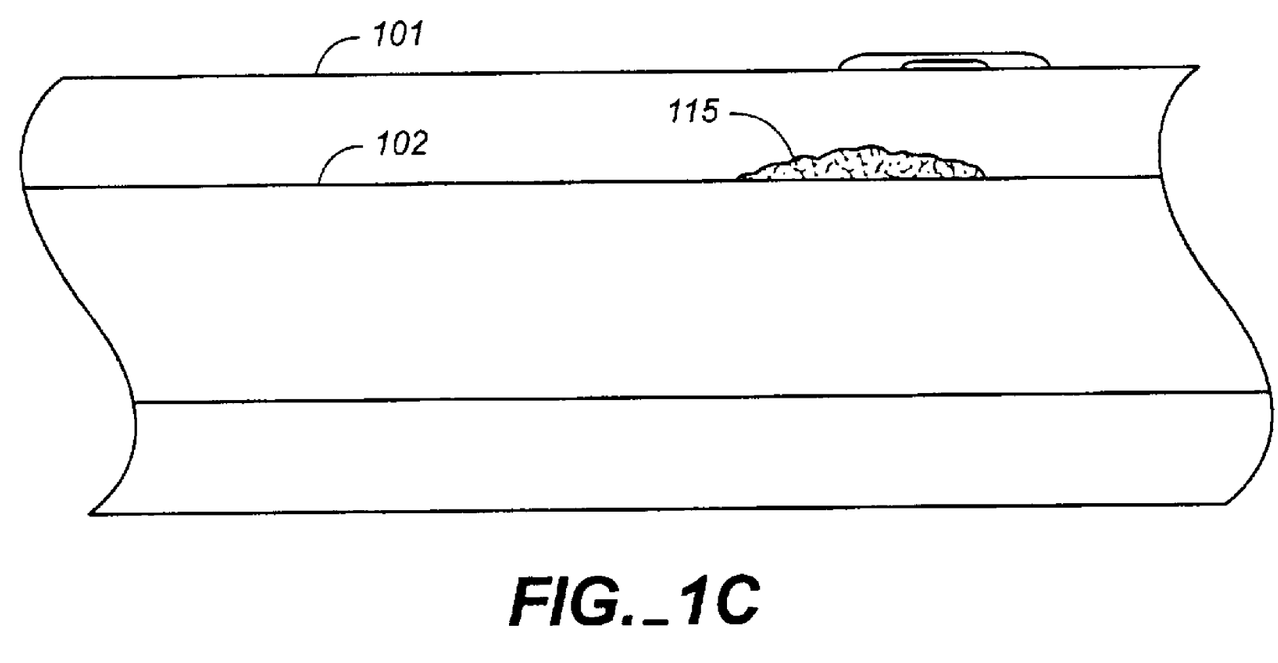
FIG. 1C illustrates the surgical sealant sealing the puncture after removal of the system of FIGS. 1A and 1B.

After injection of surgical sealant 115, sheath introducer 100, plug 110, and flexible guidewire 130 are removed. Surgical sealant 115 seals the puncture and minimizes any blood flow from body lumen 102 through the puncture (FIG. 1C).

This method and novel sheath introducer apply the surgical sealant to exactly the area to be closed. The method and sheath introducer can be used with patients with poor blood-clotting capability. The prior art problems associated with the access site are minimized. No specialized membranes or membrane delivery devices are required to form the seal. As explained more completely below, in one embodiment, if bleeding occurs following the surgical sealant injection procedure, the physician can easily recover.

A standard sheath introducer is modified by forming at least one through-wall hole 105 in a body of the sheath introducer. At least one through-wall hole 105 extends from an outer surface of the body of sheath introducer 100 to an inner surface of the body of sheath introducer 100.

Sheath introducer 200A (FIG. 2A) has a body region 210A that includes a plurality of through-wall holes 205AA, 205AB, 205AC. Plurality of through-wall holes 205AA, 205AB, 205AC are located at about a predefined distance X from a distal end tip 206A of sheath introducer 200A.

Figure 2A:
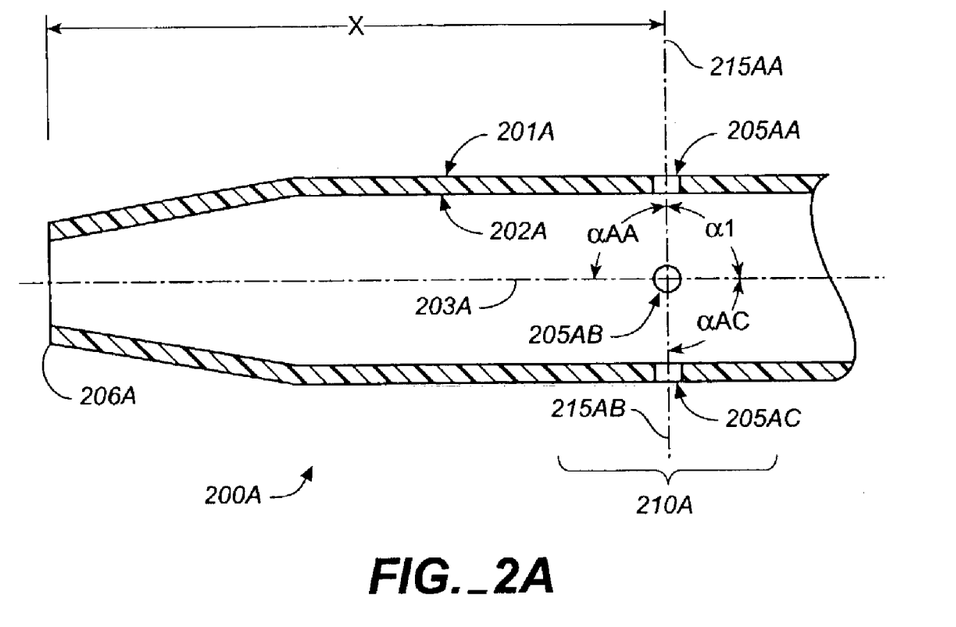
FIG. 2A is a cross-section view of one embodiment of a distal end of a sheath introducer that includes a distal end tip and a body region having a plurality of through-walls holes located at about a predefined distance from the distal end tip.

Body region 210A has an outer surface 201A separate and removed from an inner surface 202A. Outer surface 201A and inner surface 202A are orientated about a longitudinal axis 203A.

Body region 210A is cylindrical in shape. Alternatively, body region 210A is ellipsodal. The particular shape of body region 210A is not essential to this invention.

Each of through-wall holes 205AA, 205AB, 205AC (FIG. 2A) has a longitudinal axis 215AA, 215AB, 215AC(not shown) that is orientated at a predefined angle $\alpha Ai$, where i is A, B, C, with respect to longitudinal axis 203A of body region 210A. Predefined angle $\alpha Ai$ can be 90°, 60°, or any other suitable angle. Predefined angle $\alpha Ai$ can be the same for some or all through-wall holes, or different for each through-wall hole. For example, each of through-wall holes 205AA, 205AB, 205AC is orientated at the same predefined angle $\alpha 1$ to longitudinal axis 203A of region 204A, which in the embodiment of FIG. 2A is 90°.

Sheath introducer 200B (FIG. 2B) has a body region 210B that includes a plurality of through-wall holes 205BA, 205BB, 205BC. Plurality of through-wall holes 205BA, 205BB, 205BC are located at about a predefined distance X from a distal end tip 206B of sheath introducer 200B.

Figure 2B:
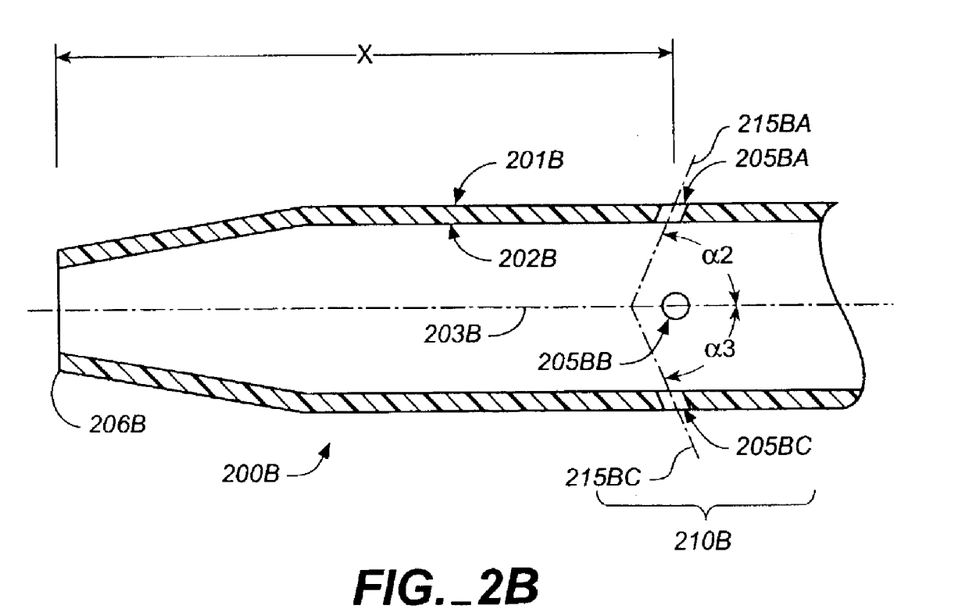
FIG. 2B is a cross-section view of another embodiment of a distal end of a sheath introducer that includes a distal end tip and a body region having a plurality of through-walls holes located at about a predefined distance from the distal end tip.

Body region 210B has an outer surface 201B separate and removed from an inner surface 202B. Outer surface 201B and inner surface 202B are orientated about a longitudinal axis 203B.

In sheath introducer 200B (FIG. 2B), not all of through-wall holes 205BA, 205BB, 205BC are orientated at the same predefined angle to longitudinal axis 203B of body region 210B. For example, through-wall hole 205BA (FIG. 2B) has a longitudinal axis 215BA that is orientated at a predefined angle $\alpha 2$ with respect longitudinal axis 203B of body region 210B. Through-wall hole 205BC (FIG. 2B) has a longitudinal axis 215BC that is orientated at a predefined angle $\alpha 3$ with respect longitudinal axis 203B of body region 210B.

In general, through-wall holes 205AA, 205AB, 205AC, 205BA, 205BB, 205BC are oriented to facilitate disbursement of the sealant so that upon withdrawal of sheath introducer 100, the sealant seals the puncture. The number of through-wall holes, the orientation of the through wall-holes, the size and shape of the through wall-holes are determined empirically.

Figure 2C:
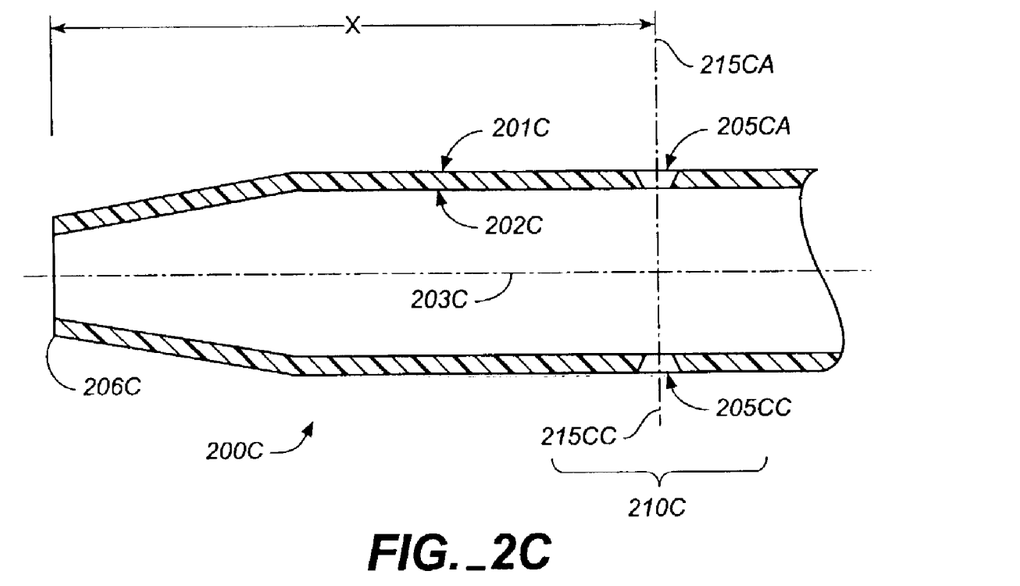
FIG. 2C is a cross-section view of still another embodiment of a distal end of a sheath introducer that includes a distal end tip and a body region having a plurality of through-walls holes located at about a predefined distance from the distal end tip.

In FIGS. 2A and 2B, each of through-wall holes 205AA, 205AB, 205AC, 205BA, 205BB, 205BC has a uniform circular cross-section about the longitudinal axis of the through-wall hole. Through-wall holes 205CA and 205CC (FIG. 2C) are tapered. Hence, the through-wall hole has a circular cross section that varies along the longitudinal axis of the through-wall hole. In FIG. 2C, the circular cross section increases going from inner surface 202C to outer surface 201C. Alternatively, the circular cross section decreases going from inner surface 202C to outer surface 201C.

Sheath introducer 200C (FIG. 2C) has a body region 210C that includes a plurality of through-wall holes 205CA, 205CB, 205CC. Plurality of through-wall holes 205CA, 205CB, 205CC are located at about a predefined distance X from a distal end tip 206C of sheath introducer 200C.

Body region 210C has an outer surface 201C separate and removed from an inner surface 202C. Outer surface 201C and inner surface 202C are orientated about a longitudinal axis 203C.

Sheath introducer 200D (FIG. 2D) has a body region 210D that includes a plurality of through-wall holes 205DA, 205DB, 205DC. Plurality of through-wall holes 205DA, 205DB, 205DC are located at about a predefined distance X from a distal end tip 206D of sheath introducer 200D.

Figure 2D:
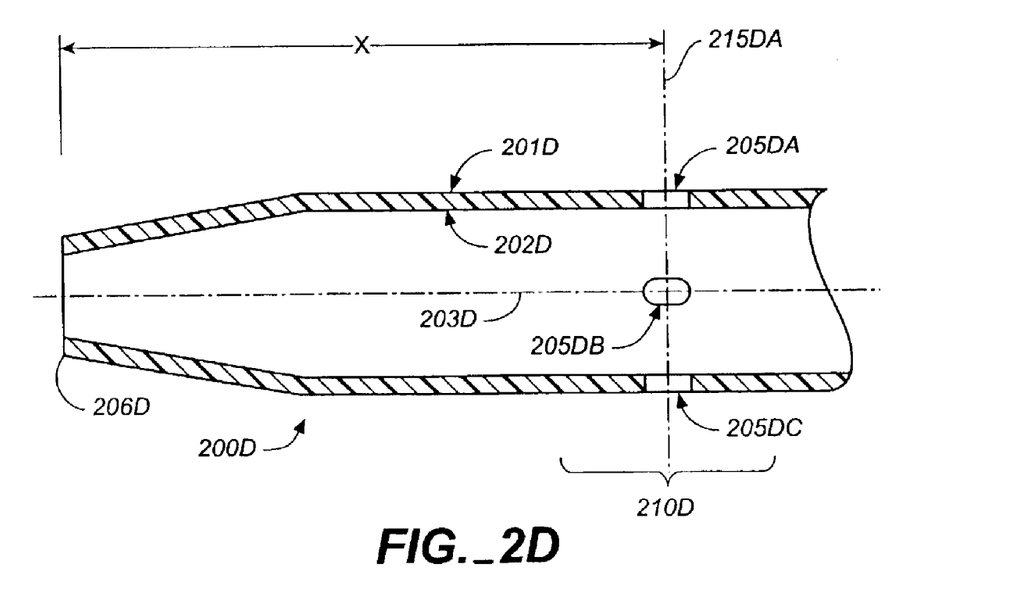
FIG. 2D is a cross-section view of still yet another embodiment of a distal end of a sheath introducer that includes a distal end tip and a body region having a plurality of through-walls holes located at about a predefined distance from the distal end tip.

Body region 210D has an outer surface 201D separate and removed from an inner surface 202D. Outer surface 201D and inner surface 202D are orientated about a longitudinal axis 203D.

In FIG. 2D, each of through-wall holes 205DA, 205DB, 205DC has a uniform elliptical cross-section about the longitudinal axis of the through-wall hole. In view of this disclosure, other through-wall hole shapes including ovals, rectangles, squares, etc. could be used. Also, a combination of shapes and angular orientations of the longitudinal axes of the through-holes could be used. A grid of through-wall holes could be formed about body region 210D. Irrespective of the pattern, shape, number, and orientation of the through-wall holes included in body region 210D, body region 210D includes at least one through-wall hole.

Figure 3A:
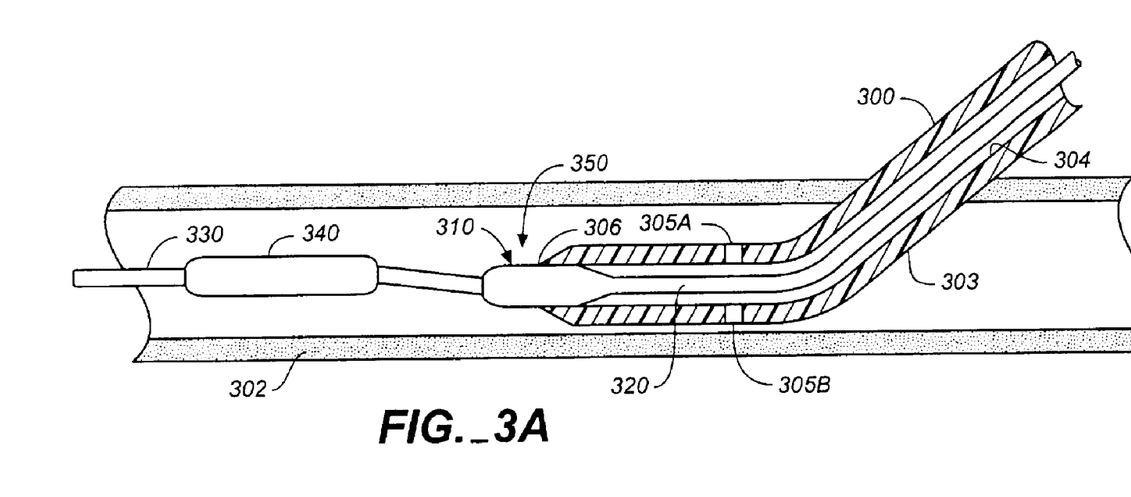
FIG. 3A is an illustration of a system that includes a sheath introducer with at least one through-wall hole, a dilator with a plug, a balloon clamp catheter, and a spring guidewire in an initial position of a puncture sealing process.
Figure 4:
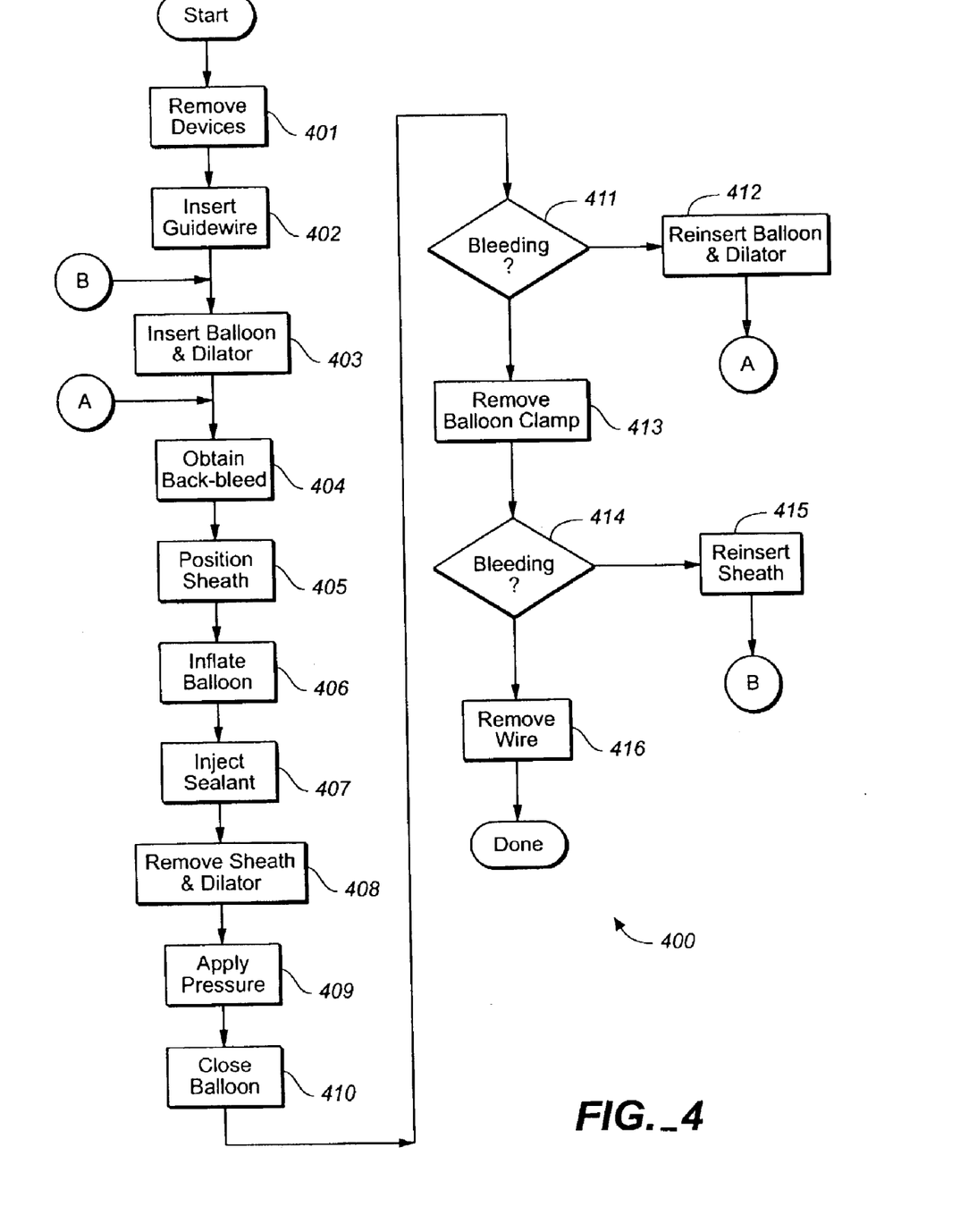
FIG. 4 is a process flow diagram of a puncture sealing process.

A system 350 (FIG. 3A) includes sheath introducer 300 with a body region that includes at least one through-wall hole, e.g., holes 305A, 305B, a dilator 320 including a dilator plug 310, a balloon clamp catheter 340, a low profile spring guidewire 330, a sealant injection system 120 (FIG. 1A), and a sealant. System 350 is used with a puncture sealing process 400 (FIG. 4).

In remove devices operation 401, all devices used in the medical procedure are removed from sheath introducer 300. Upon completion of remove devices operation 401, a low profile spring guidewire 330 is inserted into lumen 302, which is for example the femoral artery, through sheath introducer 300 in insert guidewire operation 402. Low profile spring guidewire 330 is a 0.035-inch (0.089 cm) spring guidewire and alternatively is a 0.025-inch (0.064 cm) spring guidewire.

Figure 5:
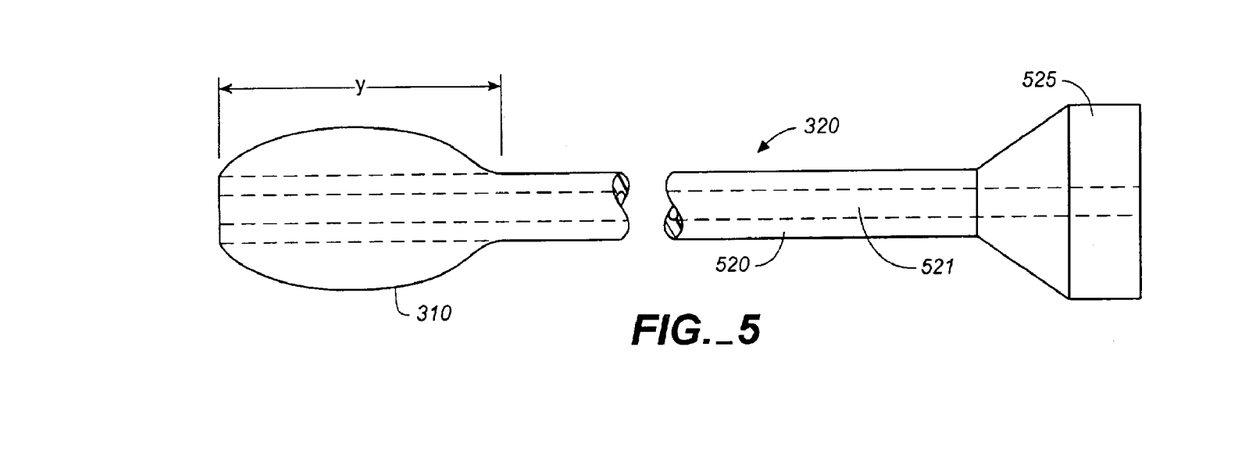
FIG. 5 is an illustration of a dilator and plug used in of the system of this invention.

Following completion of insert guidewire operation 402, balloon clamp catheter 340 and dilator 320 with dilator plug 310 are inserted into sheath introducer 300 in insert balloon and dilator operation 403. FIG. 5 is a more detailed illustration of dilator 320 with dilator plug 310.

In the example of FIG. 5, dilator 320 includes a dilator shaft 520 and a dilator hub 525. Dilator hub 525 functions as a stop. Shaft 520 is hollow so that an open inner lumen is maintained when dilator 320 and sheath introducer 300 are removed. Shaft 520 and dilator hub 525 are made from a standard material such as polyethylene.

Dilator plug 310 is formed, e.g., molded, about an outer surface of shaft 520. Dilator plug 310 extends about a predefined distance Y from a distal end of shaft 520. In one embodiment, distance Y is selected so that dilator plug 310 extends at least to distal end 306 of sheath introducer 300 and terminates so that dilator plug 310 does not block through-wall holes 305A, 305B when dilator 320 is in the deployed position.

Dilator plug 310 is made from a hydrogel material or any other material that swells to form a hermetic seal with inner surface 304 at the distal end of sheath introducer 300. Immediately before the start of insert balloon and dilator operation 403, dilator plug 310 is wet with saline to start the swelling of dilator plug 310, and then immediately inserted into the sheath.

To assist in positioning dilator plug 310 properly within sheath introducer 300 in insert balloon and dilator operation 403, a stop (See element 125 in FIG. 1A.) is mounted on a proximal end of dilator 320 so that dilator plug 310 is positioned properly at the distal end of sheath introducer 300, as illustrated in FIG. 3A. The stop may be removable. Typically, dilator 320 is configured for a specific sheath introducer 300 so that dilator plug 310 is properly positioned.

Guidewire 330 and balloon clamp catheter 340 fit within inner lumen 521 of dilator 320. Balloon clamp catheter 340 fits over guidewire 330 and in this embodiment has a size of 3 to 4 French. The balloon is manufactured from a compliant material and is sized to occlude entire femoral artery 302 when inflated. The compliant material helps to minimize femoral artery trauma.

Upon completion of insert balloon and dilator operation 403, system 350 is configured as illustrated in FIG. 3A. When dilator plug 310 swells to seal the distal end of sheath introducer 300, blood flow is blocked into distal end tip 306. However, as described above, dilator plug 310 transitions to shaft 520 of dilator 320 so that though-wall holes 305A, 305B are not blocked. Hence, blood flows into sheath introducer 300 via through-wall holes 305A, 305B up to a side port (not shown) of system 350.

Figure 3B:
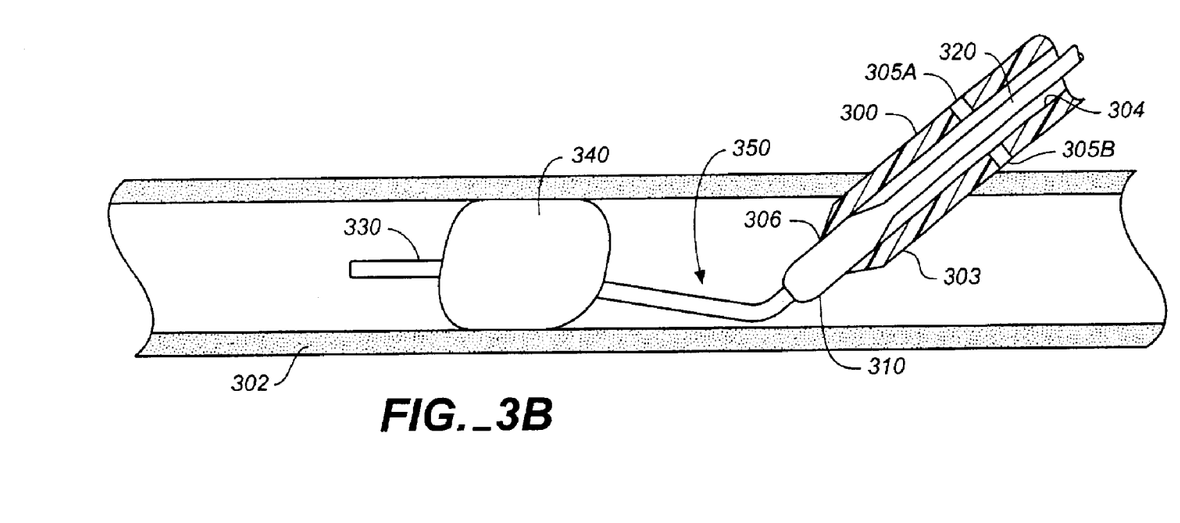
FIG. 3B is an illustration of the system of FIG. 3A in a position for surgical sealant injection in the puncture sealing process.

In obtain back-bleed operation 404, the side port is opened to obtain a back-bleed. In position sheath operation 405, sheath introducer 300 is slowly withdrawn from femoral artery 302. When the back-bleed stops, through-wall holes 305A, 305B are positioned outside the inner wall of femoral artery 302, e.g., external to the body lumen, as illustrated in FIG. 3B.

Figure 3C:
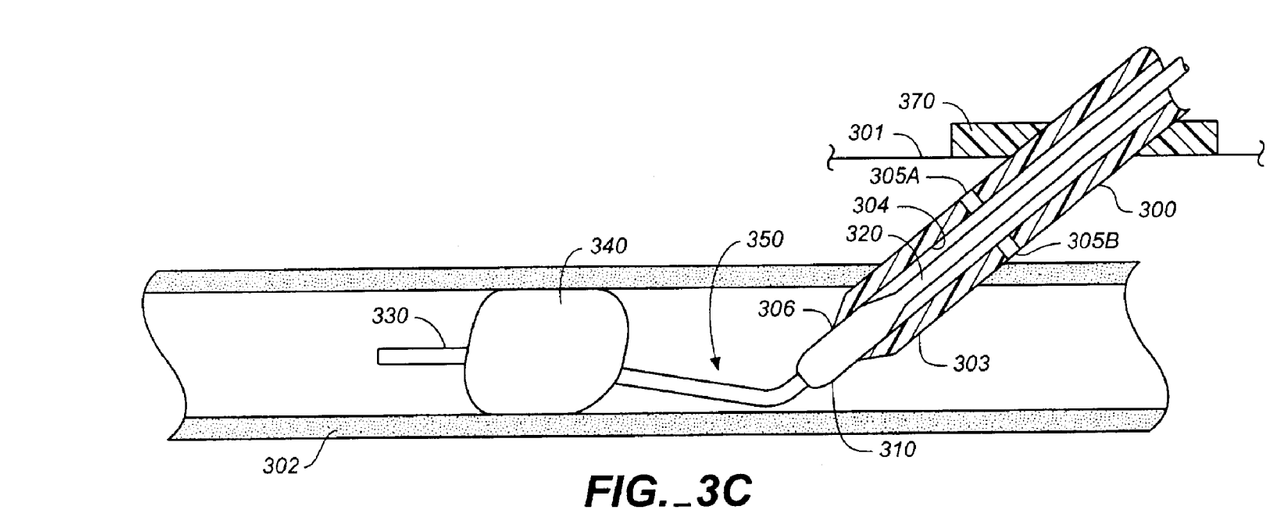
FIG. 3C is an illustration of the system of FIG. 3B that includes a clamp for maintaining the position of the sheath introducer during the surgical sealant injection in the puncture sealing process.

At this point, it is important to assure that sheath introducer 300 does not move. In FIG. 3C, a clamp 370 is placed about sheath introducer 300 at the level of skin 301. Also, there may be graduations marks on outer surface 303, i.e., a plurality of depth indicators, that can be used to assure that sheath introducer 300 is not moved after the back-bleed stops. The graduations may be used with or without clamp 370.

After sheath introducer 300 is positioned so that the back-bleed is stopped, the balloon of balloon clamp catheter is inflated in inflate balloon operation 406. The inflated balloon stops flow through femoral artery 302 and acts like manual compression.

Figure 3D:
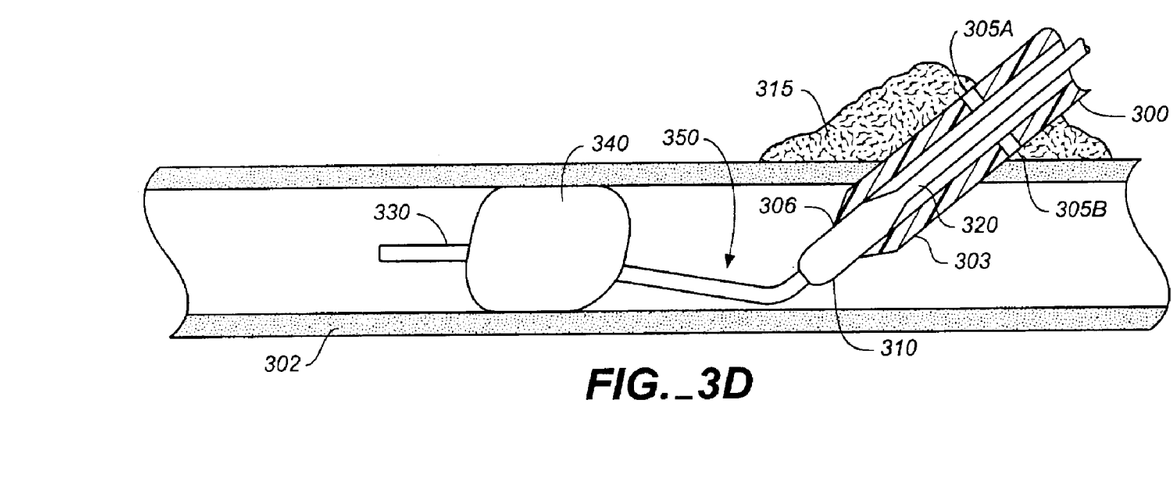
FIG. 3D is an illustration of the system of FIG. 3C following surgical sealant injection in the puncture sealing process.

In inject sealant operation 407, sealant injection system 120 is used to inject a surgical sealant 315 (FIG. 3D) through sheath introducer 300 and out through-wall holes 305A, 305B into an area about sheath introducer 300 outside femoral artery 302.

The surgical sealant is in either a fluid or a slurry form. Surgical sealants are known to those of skill in the art. Suitable surgical sealants include fibrin glue, collagen slurries, and cellulose slurries. There are also commercial sealants available from companies such Davol, Inc. that provides, for example, Avitene® Microfibrillar Collagen. The surgical sealant is non-adherent or at most very weakly adherent to sheath introducer 300.

Figure 3E:
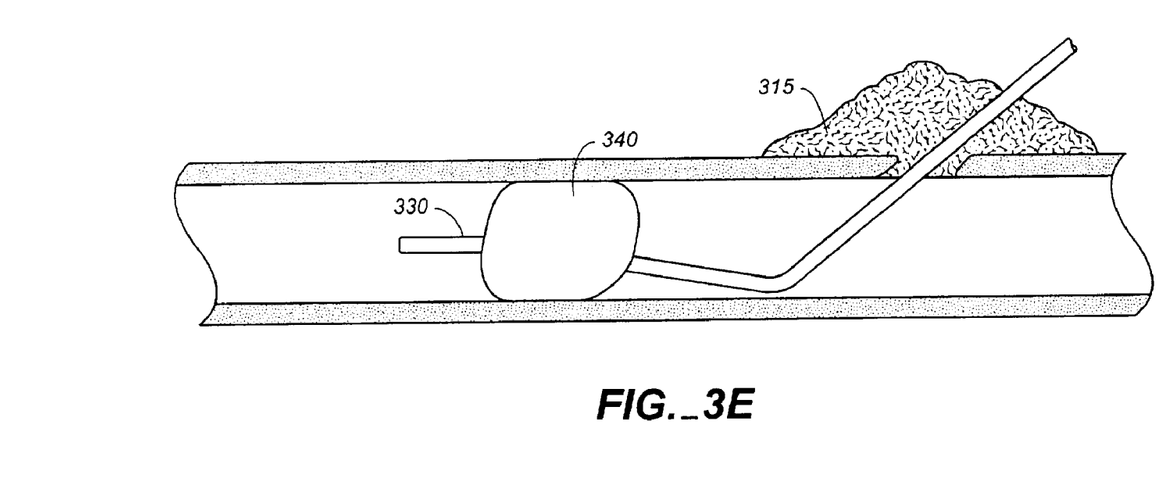
FIG. 3E is an illustration of the system of FIG. 3D following removal of the sheath introducer and dilator in the puncture sealing process.

Upon completion of inject sealant operation 407, sheath introducer 300 and dilator 320 are removed in remove sheath and dilator operation 407. At this point, surgical sealant 315 has not set up completely and so flows to fill the void left by sheath introducer 300.

In apply pressure operation 409, pressure is applied at the skin level while surgical sealant 315 hardens. Typically, this is done for several minutes. The time is determined by the type of surgical sealant 315. Surgical sealant 315 should be firm enough to curtail bleeding but not so hard as to prevent removal of balloon clamp catheter 340 and guidewire 330.

Upon completion of apply pressure operation 409, the balloon is deflated in close balloon operation 410. After the balloon is deflated, bleeding is checked in bleeding check operation 411. If bleeding is detected, the sheath and dilator are reinserted in reinsert sheath operation 412 and then operations 404 to 411 are repeated. If bleeding is not detected, balloon clamp catheter 340 is removed in remove balloon clamp operation 413.

Following removal of balloon clamp catheter 340, bleeding is again checked in bleeding check operation 415. If bleeding is detected, the sheath introducer is reinserted in reinsert sheath operation 415 and operations 403 to 414 repeated as appropriate. If no bleeding is detected, the guidewire is removed in remove wire operation 416 and process 400 is completed.

The puncture in femoral artery 302 has been sealed with the surgical sealant as illustrated in FIG. 1C. The surgical sealant has been applied to exactly the area to be closed. Also, process 400 does not depend upon the clotting capability of the patient.

Structure 350 and process 400 reduces access site complications. Therefore, a patient, who in the past might suffer such complications, no longer must undergo an invasive surgery to prevent the injury or injuries associated with such complications.

I claim:

1. A structure comprising:
   a sheath introducer having a distal end tip, said sheath introducer comprising:
   a body region at about a predefined distance from said distal end tip, said body region comprising:
   a wall bounded by an outer wall surface of said sheath introducer and by an inner wall surface of said sheath introducer wherein said body region is oriented about a longitudinal axis of said body region; and
   at least one through-wall hole extending from said outer wall surface to said inner wall surface and having a longitudinal axis oriented at an angle to said longitudinal axis of said body region; and
   a dilator comprising:
   a shaft having a distal end; and
   a dilator plug formed about said shaft and extending from about said distal end of said shaft to about a predefined distance from said distal end of said shaft wherein following insertion of said dilator into said sheath introducer, said dilator plug forms a seal in said distal end of said sheath introducer, and further wherein said predefined distance is selected so that said dilator plug does not block said at least one through-wall hole.

2. The structure of claim 1 wherein said body region further comprises:
   a plurality of through-walls holes including said at least one through-wall hole.

3. The structure of claim 1 wherein said angle is about a 90° angle.

4. The structure of claim 1 wherein said angle is other than a 90° angle.

5. The structure of claim 1 wherein said at least one through-wall hole has a uniform cross section along said longitudinal axis of said at least one through-wall hole.

6. The structure of claim 1 wherein said at least one through-wall hole has a non-uniform cross section along said longitudinal axis of said at least one through-wall hole.

7. The structure of claim 1 wherein said body region comprises a cylindrical body region.

8. The structure of claim 1 further comprising:
   a balloon clamp catheter extending through said sheath introducer.

9. The structure of claim 1 further comprising:
   a guidewire extending through said sheath introducer.

10. The structure of claim 1 further comprising:
    a surgical sealant delivery system coupled to said sheath introducer to inject a surgical sealant into said sheath introducer.

11. The structure of claim 1 wherein said sheath introducer further comprises:
    a plurality of depth indicators on said outer surface.

12. A system comprising:
    a sheath introducer having a distal end tip, said sheath introducer comprising:
    a body region at about a predefined distance from said distal end tip, said body region comprising:
    a wall bounded by an outer wall surface of said sheath introducer and by an inner wall surface of said sheath introducer wherein said body region is oriented about a longitudinal axis of said body region; and
    at least one through-wall hole extending from said outer wall surface to said inner wall surface and having a longitudinal axis oriented at an angle to said longitudinal axis of said body region;
    a dilator comprising:
    a shaft having a distal end; and
    a dilator plug formed about said shaft and extending from about said distal end of said shaft to about a predefined distance from said distal end of said shaft,
    wherein following insertion of said dilator into said sheath introducer, said dilator plug forms a seal in said distal end of said sheath introducer, and further wherein said predefined distance is selected so that said dilator plug does not block said at least one through-wall hole;
    a balloon clamp catheter extending through said sheath introducer;
    a guidewire extending through said sheath introducer; and
    a surgical sealant delivery system coupled to said sheath introducer to inject a surgical sealant into said sheath introducer.

13. The system of claim 12 wherein said body region further comprises:
    a plurality of through-walls holes including said at least one through-wall hole.

14. The system of claim 12 wherein said at least one through-wall hole has a uniform cross section along said longitudinal axis of said at least one through-wall hole.

15. The system of claim 14 wherein said at least one through-wall hole has a non-uniform cross section along said longitudinal axis of said at least one through-wall hole.

16. The system of claim 12 wherein said body region comprises a cylindrical body region.

* * * * *